United States Patent [19]

Kluger et al.

[11] Patent Number: 5,334,707

[45] Date of Patent: Aug. 2, 1994

[54] USE OF ACYL PHOSPHATE ESTERS IN THE MODIFICATION OF HEMOGLOBIN

[76] Inventors: Ronald H. Kluger, 14 Bradgate Road, Don Mills, Ontario, Canada, M3B 1J7; Andrew S. Grant, Via Oronco 27, Varese, 21100, Italy

[21] Appl. No.: 944,914

[22] Filed: Sep. 15, 1992

Related U.S. Application Data

[62] Division of Ser. No. 493,524, Mar. 14, 1990, abandoned.

[51] Int. Cl.$^5$ .................... C07K 13/00; A61K 35/14
[52] U.S. Cl. .................... 530/385; 530/402; 530/410
[58] Field of Search ............ 530/385, 402, 410

[56] References Cited

U.S. PATENT DOCUMENTS

| | | | |
|---|---|---|---|
| 2,625,536 | 1/1953 | Kirby | 260/278 |
| 3,835,203 | 9/1974 | Silbert et al. | 558/153 |
| 4,001,200 | 4/1977 | Bonsen et al. | 530/385 |
| 4,001,401 | 1/1977 | Bonsen et al. | 530/385 |
| 4,053,590 | 10/1977 | Bonsen et al. | 530/385 |
| 4,061,736 | 12/1977 | Morris et al. | 530/385 |
| 4,473,496 | 9/1984 | Scannon | 530/385 |
| 4,529,719 | 7/1985 | Tye | 530/385 |
| 4,584,130 | 4/1986 | Bucci et al. | 530/385 |
| 4,598,064 | 7/1986 | Walder | 530/385 |
| 4,600,531 | 6/1986 | Walder | 530/385 |
| 4,650,786 | 3/1987 | Wong | 530/385 |
| 4,670,417 | 6/1987 | Iwasaki | 530/385 |
| 4,710,488 | 12/1987 | Wong | 530/385 |
| 4,777,244 | 10/1988 | Bonhard et al. | 530/385 |
| 4,857,636 | 8/1989 | Hsia | 530/385 |
| 4,900,816 | 2/1990 | Wong | 530/385 |

FOREIGN PATENT DOCUMENTS

| | | |
|---|---|---|
| 0361720 | 4/1990 | European Pat. Off. |
| 1044073 | 11/1958 | Fed. Rep. of Germany |

OTHER PUBLICATIONS

Ueno et al., "Inhibition of Gelation of Extracellular . . . " Biochemistry, vol. 26, (1987) pp. 3125–3129.
Ueno, H. et al., "Effects of Methyl Acetyl Phosphate on Hemoglobin . . . ", Prog. Clin. Biol. Res., (1987), 240, pp. 105–110.
Walsh, Enzymatic Reaction Mechanisms W. H. Freeman Co.: New York, 1979.

(List continued on next page.)

*Primary Examiner*—Michael G. Wityshyn
*Assistant Examiner*—C. Sayala
*Attorney, Agent, or Firm*—Ridout & Maybee

[57] ABSTRACT

A process for the preparation of acyl phosphate esters of the formula I or salts thereof:

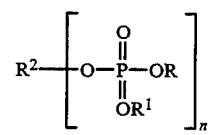

wherein
R and $R^1$ are the same or different and represent a linear or branched alkyl group having up to 4 carbon atoms, phenyl or benzyl;
n is an integer;
when n is 1, $R^2$ represents the group

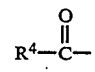

wherein $R^4$ is a linear or branched alkyl, alkenyl or alkynyl, a cyclic alkyl, a cyclic alkenyl, or aryl which may be substituted by alkyl, alkenyl, alkynyl, aryl, arylalkyl, or arylalkenyl, or.
when n is at least 2, $R^2$ represents the group

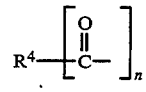

wherein $R^4$ is as defined above.

Novel compounds of the formula I wherein n is at least 2, and modified hemoglobin obtained using the novel compounds are also provided.

12 Claims, 4 Drawing Sheets

U.S. PATENT DOCUMENTS

Jencks & Carriuolo, J. Biol. Chem. 234:1272, 1959.
Di Sabato & Jencks, J. Am. Chem. Soc. 83:4400, 1961.
Oestreich & Jones, Biochem. 5:2926, 1966.
Oestreich & Jones, Biochem. 6:1515, 1967.
Briggs et al., J. Chem. Soc. (B), 1008, 1970.
Berg, J. Biol. Chem. 233:608, 1958.
Kluger & Tsui, J. Org. Chem. 45:2723, 1980.
Kluger & Tsui, Biochem. and Cell Bio. 64:434, 1986.
Whetstone, Chem. Abstr. 48:8250, 1954.
Kluger & Wasserstein, Biochem. 11:1544, 1972.
Avison, J. Chem. Soc. 732, 1955.
Klinman & Samuel, Biochem. 10L2126, 1971.
Ueno et al., Arch. Biochem. Biophys. 244:795, 1986.
Kern et al., Biochem. 24:1321, 1985.
Ueno et al., J. Biol. Chem. 264:12344, 1989.
Morrison & Boyd, Organic Chemistry, 3d ed. p. 672.
Perutz, Nature 228:726, 1970.
Toland et al., J. Am. Chem. Soc. 75:2263, 1953.
Meister, Enzymology 6:751.
J. Org. Chem. 1990, 55(9) 2864–2868.
Biomaterials Artificial Cells and Artificial Organs, vol. 17 No. 5, May 16–19, 1989 at p. 643.
Chem. Abstr. (1961) 55 (3), No. 2491.
Snyder et al. Proc. Natl. Acad. Sci. U.S.A. 84:7280, 1987.
Chatterjee et al. J. Biol. Chem. 261:9929, 1986.
Kavanaugh et al. Haem. Proc. Int. Meeting London 1986 Acta 78:99, 1987.
Kavanaugh et al. Biochem. 27:1804, 1988.
Benesch and Benesch Methods in Enzymol. 76:147, 1981.
Benesch and Kwong Biochem. Biophys. Res. Comm. 156:9, 1988.
Yang and Olsen, Biochem. Biophys. Res. Comm. 174:733, 1989.
Kluger et al. J. Org. Chem. 55:2864, 1990.
Jones et al. Biomaterials, Artificial Cells and Artificial Organs 17:643, 1989.
Manning et al. Proc. Natl. Acad. Sci. 88:3329, 1991.
Shibayama et al., Biochem. 30:8158, 1991.
Vandergriff and Winslow Chemistry and Industry Jul., 1991.
Yang and Olsen, Biochem. Biophys. Res. Comm. 174:518, 1991.
Benesch et al., Biochemistry 11:3576, 1972.
Pool, Science 250:1655, 1990.

USE OF ACYL PHOSPHATE ESTERS IN THE MODIFICATION OF HEMOGLOBIN

RELATED APPLICATION

This application is a division of Ser. No. 07/493,524 filed Mar. 14, 1990, now abandoned entitled NOVEL PROCESS FOR THE PREPARATION OF ACYL PHOSPHATE ESTERS, NOVEL ACYL PHOSPHATE ESTERS AND THEIR USE IN THE MODIFICATION OF PROTEINS.

BACKGROUND OF THE INVENTION

The present invention relates to a process for the preparation of acyl phosphate esters, novel acyl phosphate esters and their use in the preparation of modified proteins.

Acyl phosphates (mixed anhydrides of a carboxylic acid and phosphoric acid) occur as intermediates in many biochemical processes. The acyl phosphates may function as activated carboxylic acids thus promoting the transfer of the acyl group to an acceptor. For example, in the formation of intramitochondrial acyl-coenzyme A in some organisms, acetate is activated by acetate kinase through reaction with ATP to produce acetyl phosphate prior to transfer of the acetyl group to coenzyme A. (Walsh, C. Enzymatic Reaction Mechanisms, W. H. Freeman Co.: New York, 1979 pp. 234–238). Amino acids are activated as aminoacyl adenylates prior to their incorporation into peptides and proteins on ribosomes (Ibid, pp. 241–248).

The procedures reported for preparing acyl phosphate esters have many limitations. Phenyl acetyl phosphate has been prepared from phenyl phosphate and acetic anhydride (Jencks, W. P.; Carriuolo, J., J. Biol. Chem, 1959, 234, 1272, 1280; DiSabato, G., Jencks, W. P., J. Am Chem. Soc. 1961, 83, 4400; Oestreich, C. H., Jones, M. M., Biochemistry 1966, 5, 2926; Oestreich, C. H., Jones, M. M. Biochemistry 1967, 6, 1515; Briggs, P. J. et al, J. Chem. Soc. B. 1970, 1008) but the extension of this method to the use of alkyl phosphate in place of phenyl phosphate gives impure, uncharacterized products (Jencks, W. P. Carriuolo, J., J. Biol. Chem., 1959, 234, 1272). Classical methods for the synthesis of aminoacyladenylates (coupling of . . . the N-protected amino acid with adenylic acid using dicyclohexylcarbodiimide) also gives impure products (Berg, P., J. Biol. Chem. 1958, 233, 608).

Methyl acetyl phosphate has been prepared by reacting dimethyl acetyl phosphate with sodium iodide in acetone. (Kluger, R., Tsui, W. C., J. Org. Chem. 1980, 45, 2723 and Kluger, R., Tsui W. C., Biochem. and Cell Biol. 1986, 64, 434). The synthesis of the dimethyl acetyl phosphate involves refluxing acetyl chloride and trimethyl phosphate for an extended period (Whetstone, R., U.S. Pat. No. 2,648,896; and Chem. Abstr. 1954, 48, 8250; and Kluger, R., Wasserstein, P., Biochemistry 1972, 11, 1544). However, the present inventors have found that this reaction may not be extended to more complex acid chlorides or to diacid chlorides, for example, succinyl chloride or fumaryl chloride. A potential alternative route for the preparation of dimethyl acetyl phosphate is to react an acyl halide with a dimethyl phosphate salt. Acetyl chloride has been reported to react with triethylammonium dimethyl phosphate to produce dimethyl acetyl phosphate but the material was isolated in an "impure and unstable state" (Avison, A.W.D., J. Chem. Soc. 1955, 732). A further limitation of this alternative route is that it must rigorously exclude water in order to be effective, since the diester is very reactive in water (Kluger, R., Wasserstein, P., Biochemistry 172, 11, 1544).

Monoesters of acyl phosphates have been found to be stable in neutral aqueous solutions (Klimman, J. P., Samuel, D. Biochemistry, 1971, 10, 2126) and have been reported to acetylate amino groups in sites which bind anions or proteins (Khger, R., Tsui W. C., J. Org. Chem., 1980, 45, 2723; Khger, R., Tsui W. C., Blochem. and Cell Biol. 1986, 64, 434, and Ueno, H. et al, Arch. Blochem. Biophys. 1986, 244, 795). Kern et al (Biochemistry, 1985, 24, 1321) have shown that aminoacyladenylate selectively acylates amino residues of an aminoacyl t-RNA synthetase when it is produced by the enzyme from an amino acid which is not its normal substrate. Methyl acetyl phosphate hah been found to specifically acetylate amino groups exclusively in the region of the 2-3-diphosphoglycerate binding site in hemoglobin. (Ueno H., et al, Arch. Blochem. Biophys. 1986, 244, 795 and Ueno, H. et al, 1989, 26, 12344).

SUMMARY OF THE INVENTION

The present inventors have found that acyl phosphate esters can be prepared conveniently and in high yield by the reaction of a dialkyl or diphenyl phosphate and an acyl halide in the presence of an ether solvent. The dialkyl or diphenyl acyl phosphate esters obtained are readily converted to their corresponding salts by reaction with an alkali metal halide. The inventors have also found that the process is useful in producing novel acyl phosphate esters which can be used as cross-linking agents to produce modified proteins, for example modified hemoglobins.

The present invention therefore provides a process for the preparation of acyl phosphate esters of the formula I or salts thereof wherein R and $R^1$ are the same or different and represent a linear or branched alkyl group having up to 4 carbon atoms, phenyl or benzyl;

n is an integer;

when n is 1, $R^2$ represents the group wherein $R^4$ is a linear or branched alkyl, alkenyl or alkynyl, a cyclic alkyl, a cyclic alkenyl, or aryl which may be substituted by alkyl, alkenyl, alkynyl, aryl, arylalkyl or arylalkenyl, or when n is at least 2, $R^2$ represents the group wherein n is at least 2 and R⁴ is as defined above; which comprises (a) reacting a compound of the formula II wherein R and R¹ are as defined above and R³ is a counter ion, (i) with a compound of the formula III, wherein R⁴ is as defined above and R⁵ is a leaving group which is generally known for esterification reactions, in the presence of a polar organic solvent, when a compound of the formula I wherein n is 1 is required, or,

(ii) with a stoichiometric amount of a compound of the formula IV wherein n is at least 2 and R⁴ and R⁵ are as defined above in the presence of a polar organic solvent, when a compound of the formula I wherein n is at least 2 is required, and, (b) if required, the acyl phosphate esters obtained are converted into the salts thereof.

In accordance with one embodiment of the invention, a process is provided for the preparation of acyl phosphate esters of the formula Ia or salts thereof:

wherein R and R¹ are the same or different, and represent a linear or branched alkyl group having up to 4 carbon atoms, phenyl or benzyl; R⁴ is a linear or branched alkyl, alkenyl, or alkynyl, a cyclic alkyl, a cyclic alkenyl, or aryl which may be substituted by alkyl, alkenyl, alkynyl, aryl, arylalkyl or arylalkenyl which comprises reacting a compound of the formula II wherein R and R¹ are as defined above and R³ is a counter ion, with a compound of the formula III wherein R⁴ is as defined above and R⁵ is a leaving group which is generally know for esterification reactions, in the presence of a polar organic solvent and if required, the compounds of the formula Ia obtained are converted into salts thereof. In accordance with a second embodiment of the invention, a process is provided for the preparation of acyl phosphate esters of the formula Ib or salts thereof;

wherein R and R¹ are the same or different and represent a linear or branched alkyl group having up to 4 carbon atoms, benzyl or phenyl; n is an integer being at least 2, and R⁴ is a linear or branched alkyl, alkenyl or alkynyl, a cyclic alkyl, a cyclic alkenyl or aryl which may be substituted by alkyl, alkenyl, alkynyl, aryl, arylalkyl or arylalkenyl which comprises reacting a compound of the formula II wherein R and R¹ are as defined above and R³ is a counter ion, with a compound of the formula IV wherein n is at least 2, R⁴ is a linear or branched alkyl, alkenyl, or leaving group which is generally known for esterification reactions, in the presence of a polar organic solvent, and if required, the compounds of the formula Ib obtained are converted into salts thereof.

The present invention also provides novel acyl phosphate esters of the formula Ib or salts thereof wherein R and R¹ are the same or different and represent a linear or branched alkyl group having up to 4 carbon atoms, benzyl or phenyl, n is an integer being at least 2 and R⁴ represents a linear or branched alkyl, alkenyl, or alkynyl, a cyclic alkyl, a cyclic alkenyl or aryl which may be substituted by alkyl, alkenyl, alkynyl, aryl, arylalkyl or arylalkenyl.

The invention also contemplates the use of a novel acyl phosphate ester of the formula Ib or salt thereof as defined above, as a cross-linking agent in the preparation of a modified hemoglobin.

The invention further contemplates the modified hemoglobin obtained by cross-linking hemoglobin with a novel acyl phosphate ester of the formula Ib or a salt thereof as defined above.

The invention still further contemplates a method of preparing a modified hemoglobin comprising:

(a) cross-linking hemoglobin with an acyl phosphate ester of the formula Ib or a salt thereof as defined above; and, (b) purifying the resulting hemoglobin.

DESCRIPTION OF THE DRAWINGS

The invention will be better understood with reference to the drawings in which.

DETAILED DESCRIPTION OF THE INVENTION

As mentioned hereinbefore, the present invention provides a process for the preparation of acyl phosphate esters of the formula I or salts thereof wherein R and $R^1$ are the same or different and represent a linear or branched alkyl group having up to 4 carbon atoms, phenyl or benzyl;

n is an integer;

when n is 1, $R^2$ represents the group wherein $R^4$ is a linear or branched alkyl, alkenyl, or alkynyl, a cyclic alkyl, a cyclic alkenyl or aryl which may be substituted by alkyl, alkenyl, alkynyl, aryl, arylalkyl or arylalkenyl, or when n is at least 2 $R^2$ represents the group wherein n is at least 2 and $R^4$ is as defined above; which comprises (a) reacting a compound of the formula II or a salt thereof wherein R and $R^1$ are as defined above and $R^3$ is a counter ion, (i) with a compound of the formula III, wherein $R^4$ is as defined above and $R^5$ is a leaving group which is generally known for esterification reactions in the presence of a polar organic solvent, when a compound of the formula I wherein n is 1 is required, or,

(ii) with a stoichiometric amount of a compound of the formula IV wherein n is at least 2 and $R^4$ and $R^5$ are as defined above, in the presence of a polar organic solvent, when a compound of the formula I wherein n is at least 2 is required, and,

(b) if required, the acyl phosphate esters obtained are converted into salts thereof.

In one embodiment of the invention a compound of the formula Ia wherein R, $R^1$ and $R^4$ are as defined above, is prepared using reaction step (i) set out above.

In accordance with a second embodiment of the invention a compound of the formula Ib wherein n is at least 2 and R, $R^1$ and $R^4$ are as defined above, is prepared using reaction step (ii) set out above.

The reaction using reaction step (ii) where n is 2 is generally represented by the scheme:

-continued

In the compounds of the Formula II, R and $R^1$ may be the same or different and represent a linear or branched alkyl group having up to 4 carbon atoms, phenyl or benzyl, preferably methyl, ethyl or benzyl. $R^3$ in the compound of the Formula II is a counter ion and typically is an alkali metal ion such as sodium, lithium, potassium, preferably a sodium ion.

In the compounds of the formula III and IV used in the process of the invention, $R^4$ may be a linear or branched alkyl alkenyl, or alkynyl, a cyclic alkyl, a cyclic alkenyl, or aryl which may be substituted by alkyl, alkenyl, alkynyl, aryl, arylalkyl or arylalkenyl, preferably, a linear alkyl or alkenyl, phenyl, phenylalkyl, phenylalkenyl, diphenylalkyl, diphenylalkenyl or napthyl. $R^5$ in the compounds of the formulae III and IV is a leaving group which is generally known for esterification reactions. Examples of suitable leaving groups are chloro-, bromo-, and iodo-. A general discussion of esterification reactions showing typical leaving groups may be found in Morrison, R. T. and R. N. Boyd, Organic Chemistry, 3d Ed. at pages 672-674.

For the reaction according to the invention with a compound of the formula III, (i.e. reaction step (i)) a compound of the formula II wherein R and $R^1$ are methyl or benzyl and $R^3$ is a sodium or lithium ion and a compound of the formula III wherein $R^5$ is a chloro-group are preferred. Most preferably, the compound of the formula II is sodium dimethyl phosphate and in the compound of the formula II, $R^5$ is a chloro- group.

For the reaction according to the invention with a compound of the formula IV, (i.e. reaction step (ii)) a compound of the formula II wherein R and $R^1$ are methyl and $R^3$ is a sodium or lithium ion and a compound of the formula IV wherein n is 2 to 5, $R^4$ is alkenyl, phenyl, phenylalkyl or diphenylalkenyl and $R^5$ is a chloro- group are preferred. Most preferably, the compound of the formula II is sodium dimethyl phosphate and $R^5$ is a chloro- group. A compound of the formula IV wherein n is 2 and $R^4$ together with the two carbonyl groups is fumaryl, isophthalyl, terephthalyl, stilbene 3,3'-dicarboxylic acid or stilbene 4,4'-dicarboxylic acid and $R^5$ is chloro- and a compound of the formula IV wherein n is 3 and $R^4$ together with the three carbonyl groups is 1,3,5-benzene tricarboxylic acid are most preferred.

The process according to the invention for the preparation of the compounds of the formula I is carried out in the presence of a polar organic solvent, in particular an ether solvent. Suitable ether solvents are diethyl ether, dioxane or tetrahydrofuran, preferably tetrahydrofuran.

The reaction temperature for the process can be varied within a fairly wide range. In general the process can be carried out within a temperature range from $-20°$ C. to 75° C. preferably from 20° C. to 50° C. most preferably 20° C. to 25° C.

The compounds of the formulae II, III or IV used as starting materials in the process according to the invention are known from the literature or can be prepared by methods known from the literature. For example, sodium dimethyl phosphate may be prepared from trimethyl phosphate and sodium iodide in acetone.

Depending on the temperature range, the reaction times are several hours to a few days. Typically, at temperatures in the range from 20° C. to 50° C. the reaction times are between 1 and 72 hours, preferably 48 hours. The reaction is generally carried out under normal pressure in a dry atmosphere.

For the reaction of the compound of the formula II with the compound of the formula IV (i.e. reaction step (ii)) a stoichiometric amount of a compound of the formula II is added. For example, in the preparation of a compound of the formula I wherein n is 2, two equivalents of the compound of the formula II are reacted with the compound of the formula IV.

If necessary, the products of the process may be purified by recrystallization from a suitable solvent or mixture of solvents or by column chromatography. The compounds of the formula I may be converted into their corresponding salts by reaction with an alkali metal halide, for example, sodium iodide or lithium iodide. Preferably, the compounds of the formula I are converted into their salts by reaction with a stoichiometric amount of sodium iodide in the presence of a solvent such as acetone. The conversion to the corresponding salts is generally carried out in the temperature range $-20°$ C. to 80° C., preferably 20° C. to 25° C. and the reaction times are between about 1 to 12 hours, preferably 12 hours. The invention also provides novel acyl phosphate esters of the formula Ib or salts thereof Ib wherein n is an integer being at least 2, preferably 2 to 5, R and $R^1$ are the same or different and represent a linear or branched alkyl group having up to 4 carbon atoms, phenyl or benzyl, preferably methyl, ethyl or benzyl; and $R^4$ represents a linear or branched alkyl, alkenyl or alkynyl, a cyclic alkyl, a cyclic alkenyl, or aryl which may be substituted by alkyl, alkenyl, alkynyl, aryl, arylalkyl or arylalkenyl, preferably a linear or branched alkyl or alkenyl, phenyl, benzyl, phenylalkyl, phenylalkenyl, diphenylalkyl, diphenylalkenyl or napthyl. Most preferably, in the compounds of the formula Ib or the salts thereof n is 2 to 3, R and $R^1$ are the same and represent methyl; $R^4$ represents a linear alkenyl, phenyl, diphenylalkenyl, benzyl or napthyl.

Specific examples of the compounds of the formula Ib of the present invention include:

Fumaryl bis(methyl phosphates) represented by the formula set forth below:

1, R = $CH_3$; 1a, R = Na

Isophthalyl bis(methyl phosphates) represented by the formula set out below:

2, R = CH₃; 2a, R = Na

Terephthalyl bis(methyl phosphates) which is represented by the formula set forth below:

3, R = CH₃; 3a, R = Na

Stilbene 3,3'dicarboxylic acid bis(methyl phosphates) which is represented by the formula set forth below:

4, R = CH₃; 4a, R = Na

Stilbene 4,4 '-dicarboxylic acid bis(methyl phosphates) which is represented by the formula set forth below:

5, R = CH₃; 5a, R = Na

The compounds of the formula Ib may be present in the form of their salts. In general these are salts with alkali metal halides, for example sodium iodide and lithium iodide. The salts of the compounds of the formula Ib with sodium iodide are preferred.

It will be appreciated that the radials R, R¹, and R⁴ may carry one or more identical or different substituents. Examples of suitable substituents include linear or branched alkyl, halogen, cyano, nitro, alkylthio, alkoxy, amino and hydroxy.

The compounds of the formula Ib and their salts are highly selective and react rapidly with amine nucleophiles. I t has been found that when these compounds associate with a protein they react with adjacent nucleophiles. By virtue of these properties, that is negative charge and electrophilic reactivity, the compounds of the formula Ib and their salts are suitable for use as site-directed reagents for protein modification. These compounds may also be combined with other selective electrophiles to provide reagents with further types of specificity.

The compounds of the formula Ib and their salts are particularly useful as cross-linking agents in the preparation of a modified hemoglobin which can be used as a blood substitute. Particular compounds of the formula I or their salts, may be chosen as cross-linking agents based on calculations of their size relative to the known distances from cross-linking amino groups in the 2,3-diphosphoglycerate (hereinafter DPG) binding site of human hemoglobin. (Perutz, M. F., Nature (London), 1970, 228,726 and Ueno, H. et al., Arch. Blochem. Biophys. 1986, 244, p. 795; and Ueno, H. et al., J. Biol Chem. 1989, 26, 12344). Table I shows the calculated distances of the carboxyamide derivatives of the acyl phosphates resulting from the reaction of amino groups on the protein with fumaryl bis(methyl phosphate), isophthalyl bis(methyl phosphate); terephthalyl bis(-methyl phosphate); stilbene 3,3'-dicarboxylic acid bis(-methyl phosphate); and, stilbene 4,4'-dicarboxylic acid bis(methyl phosphate).

The compounds of formula Ib or the salts thereof may be reacted with liganded (oxy-, carboxy-, carbonmonoxy-, or derivatives) and unliganded (deoxy-) hemoglobin. The hemoglobin which may be cross-linked may be human, equine, porcine, ovine, bovine, simian or fish hemoglobin.

The reaction with the compounds of the formula Ib or their salts and hemoglobin may occur at a temperature of from about 0° C. to 50° C. preferably 35° C. The pH of the reaction can vary from about 5.5 to about 10, preferably from about 5 to about 8, most preferably from about 6.8 to 7.5, with the reaction occurring in a buffer, typically 100 mM Bis-Tris buffer. The reaction time may vary but generally a sufficient degree of cross-linking occurs within 2 hours. The modified hemoglobin may then be separated from the unreacted hemoglobin and other impurities using techniques known in the literature.

The hemoglobin modified using the above described reaction has been found to be cross-linked at the DPG binding site. In particular, it has been found that in the absence of DPG, the reaction of hemoglobin with fumaryl bis(methyl phosphate) produces material that is cross-linked between β subunits (val-1 to lys-82) and between the same residues in a single β subunit as well as crosslinked between α subunits between lys-99 in each subunit. In the presence of DPG, only the α-crosslink is formed.

The compounds of the formula I and the salts thereof are highly specific for selected groups on the hemoglobin molecule resulting in a high yield of the desired modified hemoglobin product.

The modified hemoglobin as in the present invention may be used as a blood substitute or blood plasma expander. The modified hemoglobin may be combined with a pharmaceutically acceptable carrier to prepare a pharmaceutical composition. Suitable pharmaceutically acceptable carriers include physiological saline, Ringer's solution, lactated Ringer's solution, Locke-Ringer's solution, Krebs-Ringer's solution, Hartmann's balanced saline and heparinized sodium-citrate-citric acid-dextrose solution. The modified hemoglobin may also be combined with other plasma substitutes and plasma expanders. Examples of plasma substitutes are poly(ethyleneoxide), polyvinylpyrrolidone, polyvinyl alcohol and ethylene oxidepolypropylene glycol condensates and examples of plasma expanders are linear polysaccharides, including dextrans, albumin, other plasma proteins, pectins, balanced fluid gelatin and hydroxyethyl starch. The modified hemoglobin and pharmaceutical compositions containing the modified hemoglobin may be administered using conventional methods.

The following examples are further provided for illustrative purposes only and are in no way intended to limit the scope of the present invention.

EXAMPLE 1 a) Dimethyl acetyl phosphate.

Dimethyl acetyl phosphate has previously been prepared by extended refluxing of a solution of acetyl chloride and trimethyl phosphate (Whetstone, R., U.S. Pat. No. 2,648,896, 1953; Chem. Abstr. 1954, 48, 8250i; and Kluger, R., Wasserstein, P., Biochemistry 1972, 11, 1544). The reaction was accomplished much more rapidly by using acetyl bromide in place of acetyl chloride. However, the method could not be used in general since acid bromides are not accessible from more complex acid chlorides. The general method involves preparing acetyl dimethyl phosphate by dropwise addition of acetyl bromide (4 g, 32 mmol) to trimethyl phosphate (10 g, 71 mmol) at 50° C. over a period of fifteen minutes. After an additional fifteen minutes, the reaction solution was distilled at 0.30 torr through a 20 ×1 m vacuum-jacketed column. An initial low boiling fraction of the excess trimethyl phosphate was followed by the product at 55°-60° C. Yield, 4.0 g, 75%. Analysis of product: proton NMR in CC$_4$, relative to tetramethylsilane, δ2.2 (3 H, d, $J_{P-H}$=1.5 Hz), 3.75 (6 H, d, $J_{P-H}$=11 Hz). The spectrum was identical to the $^1$H spectrum of dimethyl acetyl phosphate. (Avison, A. W. D., J. Chem. Soc. 1955, 732).

b) Dimethyl acetyl phosphate.

A suspension of sodium dimethyl phosphate (14.8 g, 0.1 mmol, from trimethyl phosphate and sodium iodide in acetone) and acetyl chloride (7.8 g, 0.1 mmol) in dry tetrahydrofuran (80 mn) was stirred for two days at room temperature in a flask fitted with a drying tube. The reaction solution was filtered and the tetrahydrofuran was removed under reduced pressure. The resulting colorless liquid was Kugelrohr-distilled (Aldrich Kugelrohr apparatus, 55°-60° C. 0.30 torr) to give 14.2 g (80%) of dimethyl acetyl phosphate.

c) Methyl acetyl phosphate. Methyl acetyl phosphate was prepared from dimethyl acetyl phosphate (Kluger, R, Tsui W.-C., J. Org. Chem. 1980, 45, 2723). A solution of sodium iodide (2.4 g, 16 mmol) in dry. acetone (15 mL) was added to a solution of acetyl dimethyl phosphate (2 g, 16 mmol) in dry acetone (10 mL). The pale yellow solution stood overnight at room temperature. The precipitate was collected by filtration in a sintered-glass funnel, washed with dry acetone, followed by methylene chloride. The resulting white powder was dried under vacuum and recrystallized from hot isopropanol to give 2.2 g (80%) of the sodium salt of methyl acetyl phosphate. Analysis of product: $^1$H NMR in D$_2$O, relative, to DSS, δ2.18 (3 H, $J_{P-H}$=1.4 Hz), 3.67 (3 H, d, $J_{P-H}$=11.6 Hz). The spectrum was identical to the previously reported $^1$H NMR spectrum of methyl acetyl phosphate. (Ibid, 2723).

EXAMPLE 2

1, R = CH$_3$; 1a, R = Na (a) Fumaryl bis(dimethyl phosphate) (1)

A suspension of sodium dimethyl phosphate (6.9 g, 47 mmol from trimethyl phosphate and sodium iodide in acetone) and fumaryl chloride (3.6 g, 24 mmol) was stirred in dry tetrahydrofuran (60 mL, dried by distillation from sodium benzophenone ketyl) under nitrogen at room temperature for two days. The solution was then filtered through a sintered glass funnel and the solvent was removed, leaving the product as a solid. Recrystallization from benzene and ether yielded the product as white flakes (4.7 g, 61%, mp 76°-77° C.). Analysis of product: IR (KBr)-C=O 1743 cm$^{-1}$; $^1$H NMR (CDC$_3$) δ6.93 (H—C=C, 2 H, s), 4.05 (—OCH$_3$, 12 H, d, $J_{P-H}$=11.6 Hz). $^{13}$C NMR (CDC$_3$): δ158.12 (d, $J_{P-C}$=7.9 HZ), 134.39 (d, $J_{P-C}$=9.4 Hz), 55.39 (d, $J_{P-C}$=5.9 HZ); $^{31}$P NMR (CHC$_3$) δ-15.4 (hept, $J_{P-H}$=11.6 Hz). In the analysis of the product, proton NMR spectra were recorded on a Varian T-60 (60M Hz) spectrometer or a Varian Gemini (200M Hz) spectometer. Phosphorous spectra were recorded on a Varian XL-200 spectrometer. $^{13}$C NMR spectra were recorded on the Varian Gemini spectrometer. Infrared spectra were recorded on a Nicolet SDX FTIR spectrometer.

The reaction was repeated with the addition of 0.01 and 0.1 equivalents of 18-crown-6 (in order to increase the extent of dissolution of sodium phosphate). The yield was lower in both cases than when the crown ether was absent.

(b) Fumaryl bis(sodium methyl phosphate) (1a)

A solution of sodium iodide (0.9 g, 6 mmol) in dry acetone (6 mL) was added to an acetone (6 mL) solution of fumaryl bis(dimethyl phosphate) (1 g, 3 mmol) in a 25 mL flask. The solution was shaken and the flask was left for twelve hours, during which time the product precipitate was a pale yellow powder. Filtration, followed by washings with dry acetone and methylene chloride resulted in an off-white powder that was dried under vacuum. One gram of the material was recrystallized by dissolving in 20 mL methanol. Then 40 mL 1:1 ethanol: isopropanol was added and the solution stood for 30 min. The resulting crystals were collected and dried in vacuo (mp>200° C. 93% yield) Analysis of product: IR (KBr): C=O 1714 cm$^{-1}$. $^1$H NMR (D$_2$O) δ6.85 (H—C=C,2 H, d, J=2 Hz), 3.65 (—OCH$_3$, 6 H, d, $J_{P-H}$=12 Hz). $^{13}$C NMR (D$_2$O): δ163.0 (d, $J_{P-C}$=6.4 Hz), Anal. 135.6 (d, $J_{P-C}$=7.6 Hz), 54.76 (d, $J_{P-C}$=6.4 Hz). Anal. (C$_6$H$_8$O$_{10}$P$_2$Na$_2$) C,H,P.

The product was identified as a symmetrical monomethyl phosphate by analysis of proton-coupled $^{31}$P NMR spectra and proton NMR spectra. The proton-coupled $^{31}$P NMR spectra of the bis(dimethyl phosphates) consists of a single phosphorous signal which is a septet due to coupling of two equivalent phosphorus nuclei to equivalent sets of six protons (from the two methyl groups). Cleavage of one methyl group from each end converts the material to one whose phosphorus NMR signal is a quartet. Integration of the signal of the methoxy protons in the proton NMR spectrum, relative to that of the remaining protons in the molecule, shows that cleavage of half of the ester groups has occurred.

EXAMPLE 3

2, R = CH$_3$; 2a, R = Na

(a) Isophthalyl bis(dimethyl phosphate) (2)

isophthalyl bis(dimethyl phosphate) was prepared from isophthalyl dichloride (4.83 g, 23 mmol) and sodium dimethyl phosphate (6.9 g, 47 mmol) in dry tetrahydrofuran (50 mL) as set forth in Example 1, to produce a colorless oil in 83% yield. Analysis of product: IR (film) C=O 1754 cm$^{-1}$; $^1$H NMR (CDC$_3$) δ 8.72 (1 H, t, J=1.7 Hz), 8.35 (2 H, dd, J=1.7, 7.8 Hz), 7.68 (1 H, t, J=7.8 Hz), 4.02 (12 H, d, $J_{P-C}$=11.7 Hz). $^{13}$C NMR (CDC$_3$) δ160.60 (d, $J_{P-C}$=7.0 Hz), 137.39 (d, $J_{P-C}$=11.5 Hz), 136.94, 133.43, 130.39, 56.23 (d, $J_{P-C}$=4.8 Hz).

(b) Isophthalyl bis(sodium methyl phosphate)(2a)

Isophthalyl bis(sodium methyl phosphate) was prepared in 95% yield from isophthalyl bis(dimethyl phosphate) (1.82 g, 4.8 mmol) and sodium iodide (1.44 g, 9.6 mmol) as set forth in Example 1. Analysis of product: mp>200° C.; IR (KBr) C=O 1720 cm$^{-1}$; $^1$H NMR (D$_2$O) δ8.52 (1 H, t, J=1.8 Hz), 8.17 (2 H, dd, J=1.8, 7.9 Hz), 7.52 (1 H, t, J=7.9 Hz), 3.56 (6 H, d, $J_{P-H}$=11.4 Hz); $^{13}$C NMR (D$_2$O) δ166.40 (d, $J_{P-C}$=8.1 Hz), 138.72, 137.95 (d, $J_{P-C}$=10.0 Hz), 134.89, 132.66, 56.91 (d, $J_{P-C}$=6.2 Hz). The product was identified as a symmetrical monomethyl phosphate by analysis of proton-coupled -P NMR spectra and proton NMR spectra as set forth in Example 1.

EXAMPLE 4

3, R = CH$_3$; 3a, R = Na

(a) Terephthalyl bis(dimethyl phosphate) (3)

Terephthalyl bis(dimethyl phosphate) was prepared from terephthalyl dichloride (4.83 g, 23 mmol) and sodium dimethyl phosphate (6.9 g, 47 mmol) in dry tetrahydrofuran (50 mL) as set forth in Example 1, to give a white solid. Recrystallization from benzene with addition of ether gave crystals: mp 81°-82° C. in 91% yield. Analysis of product: IR (KBr) C=O 1743 cm$^{-1}$. $^1$H NMR (CDC$_3$) δ160.00 (d, $J_{P-C}$=7.9 Hz), 133.10 (d, $J_{P-C}$=8.6 Hz), 130.90, 55.48 (d, $J_{P-C}$=4.7 Hz).

(b) Terephthalyl bis(sodium methyl phosphate) (3a)

Terephthalyl bis(sodium methyl phosphate) was prepared in 95% yield from terephthalyl bis(dimethyl phosphate) (1 g, 2.6 mmol) and sodium iodide (0.78 g, 5.2 mmol) in acetone as set forth in Example 1. Analysis of Product: mp>200° C.; IR (KSr) C=O 1715 cm$^{-1}$; $^1$H NMR (D$_2$O) δ7.93 (4 H, s), 3.56 (6 H, d, $J_{P-H}$=11.5 Hz); $^{13}$C NMR (D$_2$O) δ166.36 (d, $J_{P-C}$=8.1 Hz), 136.63 (d, $J_{P-C}$=7.0 Hz), 133.35, 56.72 (d, $J_{P-C}$=2.6 Hz). Anal. (C$_{10}$H$_{10}$O$_{10}$P$_2$Na$_2$) CHP. The product was identified as a symmetrical monomethyl phosphate by analysis of proton-coupled $^{31}$P NMR spectra and proton NMR spectra as set forth in Example 1.

EXAMPLE 5

4, R = CH$_3$; 4a, R = Na (a) Stilbene 3,3'-dicarboxylic acid

Stilbene 3,3'-dicarboxylic acid was prepared by the method of Toland J., et al. J. Am Chem. Soc. 1953, 75, p. 2263.

(b) Stilbene 3,3'-dichloroformate:

Stilbene 3,3'-dicarboxylic acid (4.9 g, 18 mmol), thionyl chloride (50 mL) and a catalytic amount of dry dimethyl formamide (10 drops) were refluxed for twelve hours. Excess thionyl chloride (20 mL) was distilled off and the product crystallized as yellow needles. The crystals (2.53 g, 8.3 mmol, 46%) were collected by filtration, washed sparingly with ether, and pumped dry. Recrystallization from toluene gave pure material (mp 179°-181° C.). $^1$H NMR (CDC$_3$) δ3.68 (16 H, s), 7.07 (2 H, s), 7.20-7.51 (H, m).

(c) Stilbene 3,3'-dicarboxylic acid bis(dimethyl phosphate) (4)

Stilbene 3,3'-dichloroformate (2.4 g, 7.9 mmol) and sodium dimethyl phosphate (2.3 g, 15.8 mmol) were stirred at room temperature in dry tetrahydrofuran for 48 hours under nitrogen. The reaction mixture was filtered and solvent evaporated to give a solid. This was recrystallized from benzene/ether to give pure material (2.62 g, 5.4 mmol, 68% yield). Analysis of product: $^1$H NMR (CDC$_3$) d 8.19 (1 H, t, J =1.6 Hz), 7.99 (1 H, dr, J=1.6, 7.7 Hz), 7.95 (1 H, dt, J =1.6 Hz, 7.7,), 7.52 (1 H, t, J=7.7 Hz), 4.02 (12 H, d, J =11.7 Hz); $^{13}$C NMR (CDC$_3$) δ161.00 (d, $J_{P-C}$=8.3 Hz), 137.60, 32.50, 130.00, 129.33, 128.91, 128.74, 128.56 (d, $J_{P-C}$=8.5 Hz), 55.35 (d, $J_{P-C}$=5.4 Hz). Thin Layer Chromatography:R$_f$=0.29 (Silica plates, 1:1 dichloromethane: ethyl acetate).

(d) Stilbene 3,3'-dicarboxylic acid bis(sodium methyl phosphate) (4a)

Stilbene 3,3'-dicarboxylic acid bis(sodium methyl phosphate) was prepared from stilbene 3,3'-dicarboxylic acid bis(dimethyl phosphate) (3.52 g, 7.3 mmol) and sodium iodide (2.19 g, 14.6 mmol) in acetone as above in 93% yield. Analysis of product: mp>200° C., IR (KBr) C=O 1714 cm$^{-1}$; $^1$H NMR (D$_2$O) δ7.51 (2H, d, J - 7.9 Hz), 7.47 (2 H, s) 7.22 (2 H, d, J=7.9 Hz), 7.10 (12 H, t, J=7.9 Hz), 6.56 (s, 2 H), 3.62 (6 H, d, J=11.4 Hz); $^{13}$C NMR (D$_2$O) δ167.00 (d, J$_{P-C}$=8.3 Hz), 140.01, 134.88, 132.30, 132.08, 131.94, 131.76, 130.05 (d, J$_{J-C}$=8.1 Hz), 56.95. Thin Layer Chromatography:R$_f$=0.39 (Silica plates, ethanol.) The product was identified as a symmetrical monomethyl phosphate by analysis of proton-coupled $^{31}$P NMR spectra and proton NMR spectra as set forth in Example 1.

EXAMPLE 6

5, R = CH$_3$: 5a, R = Na (a) Stilbene 4,4'-dicarboxylic acid

Stilbene 4,4'-dicarboxylic acid was prepared by the method of Toland J., et al, J. Am. Chem. Soc., 1953, 75, p.2263.

(b) Stilbene 4,4'-dichloroformate.

A suspension of stilbene 4,4'dicarboxylic acid (5 g, 18.6 mmol), thionyl chloride (60 mL) and a catalytic amount of dry dimethylformamide (0.25 mL) were refluxed for 24 hours. The dicarboxylic acid did not dissolve, but was converted directly into the diacid chloride which was also largely insoluble in the reaction medium. The reaction solution was refrigerated for 12 hours. The yellow crystalline product was collected by filtration, washed sparingly with acetone and pumped to dryness (5.2 g, 17 mmol, 92% yield). Analysis of product: mp 238° C. $^1$H NMR (dimethyl sulfoxide-d$_6$) δ7.95 (4 H, d, J=10 Hz), 7.73 (4H, d, J=10 Hz), 7.48 (2 H, s).

(c) Stilbene 4,4'-dicarboxylic acid bis(dimethyl phosphate) (5)

Stilbene 4,4'-dichloroformate (2.6 g, 8.5 mmol) and sodium dimethyl phosphate (3.15 g, 21.3 mmol) were stirred in dry tetrahydrofuran at 50° C. under nitrogen for 48 hours. The reaction mixture was filtered through a sintered glass funnel and the solvent removed by evaporation to give the crude 15 product. Recrystallization from tetrahydrofuran/ether gave pure material (1.19 g, 23%). Analysis of product: mp 176°-177° C. $^1$H NMR (CDC$_3$)δ8.08 (4 H, d, J=8.5 Hz), 7.65 (4 H, d, J=8.5 Hz), 7.29 (2 H, s), 4.03 (12 H, d, J=11.7. Hz). $^{13}$C 160.5 (d, J$_{P-C}$=8.1 Hz), 142.5, 131.1, 130.5, 127.1, 127.0. 55.2 (d, J$_{P-C}$5.9 Hz). Thin layer chromatography:R$_f$=0.27 (Silica plates, 1: 1 dichloromethane/ethyl acetate).

(d) Stilbene 4,4'-dicarboxylic acid bis(sodium methyl phosphate) (5a).

Stilbene 4,4'-dicarboxylic acid bis(sodium methyl phosphate) was prepared from stilbene 4,4'-dicarboxylic acid bis(dimethyl phosphate) and sodium iodide in acetone as set forth in Example 1 Analysis of product: mp>200° C. IR (KBr) C=O 1715 cm$^{-1}$; $^1$H NMR (D$_2$O) δ7.88 (4 H, d, J=8.1 Hz), 7.27 (4 H, d, J =8.1 HZ), 6.77 (2 H, s), 3.80 (6 H, d, J=11.3 Hz); $^{13}$C NMR (D$_2$O) δ166.77 (d, J$_{P-C}$=8.3 Hz), 144.8, 133.5, 132.7, 1308 (d, J$_{P-C}$=8.1 Hz), 129.7, 56.6. -P NMR δ-2.38 (from H$_3$PO$_4$). The product was identified as a symmetrical monomethyl phosphate by analysis of proton coupled $^{31}$P NMR spectra and proton NMR spectra as set forth in Example 1.

EXAMPLE 7

Benzene 1,3,5-tricarboxylic acid tris(sodium methyl phosphate) was prepared from benzene 1,3,5-tricarboxylic acid tris(dimethyl phosphate), (prepared from sodium dimethyl phosphate and 1,3,5-benzene tricarbonyl trichloride) and sodium iodide as set forth in Example 3 by proportionally increasing the amount of the compounds used in the process.

EXAMPLE 8

The solution stability of the bis(methyl acyl phosphates) was examined. The hydrolysis of fumaryl bis(sodium methyl phosphate), stilbene 3,3'dicarboxylic acid bis(sodium methyl phosphate) and stilbene 4,4'dicarboxylic acid bis(sodium methyl phosphate) in 0.100M tris-HCL buffer, pH 7.4, 37° C., were followed by integrating signals for the reactant and the phosphorus-containing product, methyl phosphate, in the $^{31}$P NMR spectrum. Production of methyl phosphate was observed as an indication of hydrolysis or of acylation of the buffer. The half life of the fumaryl compound, was 36 hours under these conditions. The half life of the 3,3'stilbene derivative, was 100 hours. The reaction of the 4,4'stilbene derivative was followed for nine hours and there was no change observed in the spectrum over this time. This indicates that the reagents are sufficiently stable in solution and that they do not react rapidly with buffer. This is in agreement with earlier reports of the reactivity of acyl phosphate esters (Disabato, G.; Jencks, W. P., J. Am. Chem. Soc. 1961, 83, 4393, 4400).

EXAMPLE 9

Cross-linking of Hemoglobin

Solutions (2 mL) of 4,4'stilbene dicarboxylic acid bis(methyl phosphate) at concentrations of 0.3 mM, 3.0 mM, 30 mM, and 300 mM were prepared in 0.100M tris-HCL buffer pH 7.4. A control solution containing only the buffer was prepared. To each of these freshly prepared solutions, 40 mg of human hemoglobin (Sigma Chemical Company) was added so that the resulting solution was 0.3 mM in hemoglobin. The reaction mixtures were than stirred vigorously and incubated at 37° C. After four hours the solutions were dialyzed against 0.100M sodium phosphate buffer, pH 7.0, for 20 hours at 4° C. to remove the unreacted acyl phosphates. The samples were then lyophilized and analyzed by SDS-polyacrylamide gel electrophoresis to assess the extent of intersubunit cross-linking (Weber, K; Osborn, M.; J. Biol. Chem. 1969, 244, 4406). Prior to electrophoresis, the hemoglobin samples, cross-linked bovine hemoglobin standard (Sigma Dalton Mark VII-L doubly crystallized, dialyzed, lyophilized), and molecular weight standards were denatured by boiling for 15 min. in 0.11M sodium phosphate buffer, pH 7.0, which contained 1% sodium dodecyl sulfate, 1% 2-mercaptoethanol, 36% urea, and 0.015% bromphenol blue. The final protein concentrations were 2 mg/mL and 10 to 20 μL aliquots were loaded on the gel. The process was conducted using a Bio-Rad Mini-Protean II dual slab cell apparatus. The extent of cross-linking of the hemoglobin could be estimated by visual comparison of the resolved electrophoretic bands after fixation followed by staining with Coomassie Brilliant Blue R.

The above procedure was repeated with solutions of fumaryl bis(methyl phosphate) at concentrations of 0.3 mM, 3.0 mM and 30 mM; 3,3'stilbene dicarboxylic acid bis(methyl phosphate) at a concentration of 30 mM and methyl acetyl phosphate at a concentration of 0.6M.

The SDS gel electrophoresis indicated that the reaction of hemoglobin with stilbene 3,3'dicarboxylic acid bis(methyl phosphate), stilbene 4,4'-dicarboxylic acid bis(methyl phosphate), and with fumaryl bis(methyl phosphate) produced dimeric and tetrameric species. The lanes containing the hemoglobin modified with these reagents showed bands which correspond to the dimer (32,000), trimer (48,000) and tetramet (64,000) (compared with the standard cross-linked bovine hemoglobin). As well, there were trace bands of higher molecular weight. Bands for unreacted hemoglobin indicated that the material is fully dissociated into monomers. Control experiments with hemoglobin which had been reacted with methyl acetyl phosphate and with stilbene 3,3'-dicarboxylic acid gave materials which are monomeric according to the gel patterns. These results indicate that cross-linking reactions are taking place only in the presence of the difunctional acyl phosphate esters.

EXAMPLE 10

Characterization of Cross-linked Hemoglobin

The effect of pH, type of buffer, and ligand state of the cross-linked hemoglobin was examined for the reaction of fumaryl bis(methyl phosphate) (FMP) with hemoglobin. No significant differences were observed in amounts or varieties of reaction products when reacting carbonmonoxyhemoglobin (COHb) with FMP in bis-Tris compared to HEPES [4-(2-hydroxy-ethyl)-1-piperazine ethanesulphonic acid]at pH 7.5, 35°, for 2 hours. Over the range of pH from 6.8 to 7.5, the greatest reaction between COHb and FMP was obtained at the pH of 7.2 in bisTris. The reaction at pH 7.2, . 35° with 1 mM COHb and 2 mM FMP resulted in the conversion of about 75% of the hemoglobin to fumaryl derivatives in 2 hours with little further change by 3 hours. The major modified component was approximately 35% of the total hemoglobin by 10 minutes and did not change appreciably thereafter. A second peak of reacted material observed by anion exchange chromatography increased over 3 hours from 14% at 10 minutes to about 30% by 3 hours. From these results the reaction conditions were standardized to 1 mM Hb, 2 mM FMP, pH 7.2 in 100 mM bisTris, at 35° C. for 2 hours.

Structural characterization of the major and some minor modified hemoglobins that result form reacting deoxyHb and COHb with FMP were made by isolating single hemoglobin components wherever possible. The initial separation was made on a preparative size Synchropak AX300 anion exchange column. Further purification was obtained by rechromatography of anion exchange zones containing mixtures of hemoglobins on a preparative size Synchropak CM300 cation exchange column. Zones from cation exchange rechromatography were then subjected to globin chain separation using Vydak C-4 large pore reverse phase columns. In some cases, this was sufficient for identification of the unmodified globin chains. In most cases the globin chain was isolated, treated by oxidations or aminoethylation to stabilize the zysteinyl residues, hydrolyzed with trypsin and glu-C proteonase and the resultant peptides were separated and analyzed for amino acid composition. Table II lists the components isolated and the structural modifications identified for the FMP treated hemoglobin.

Figure 1:
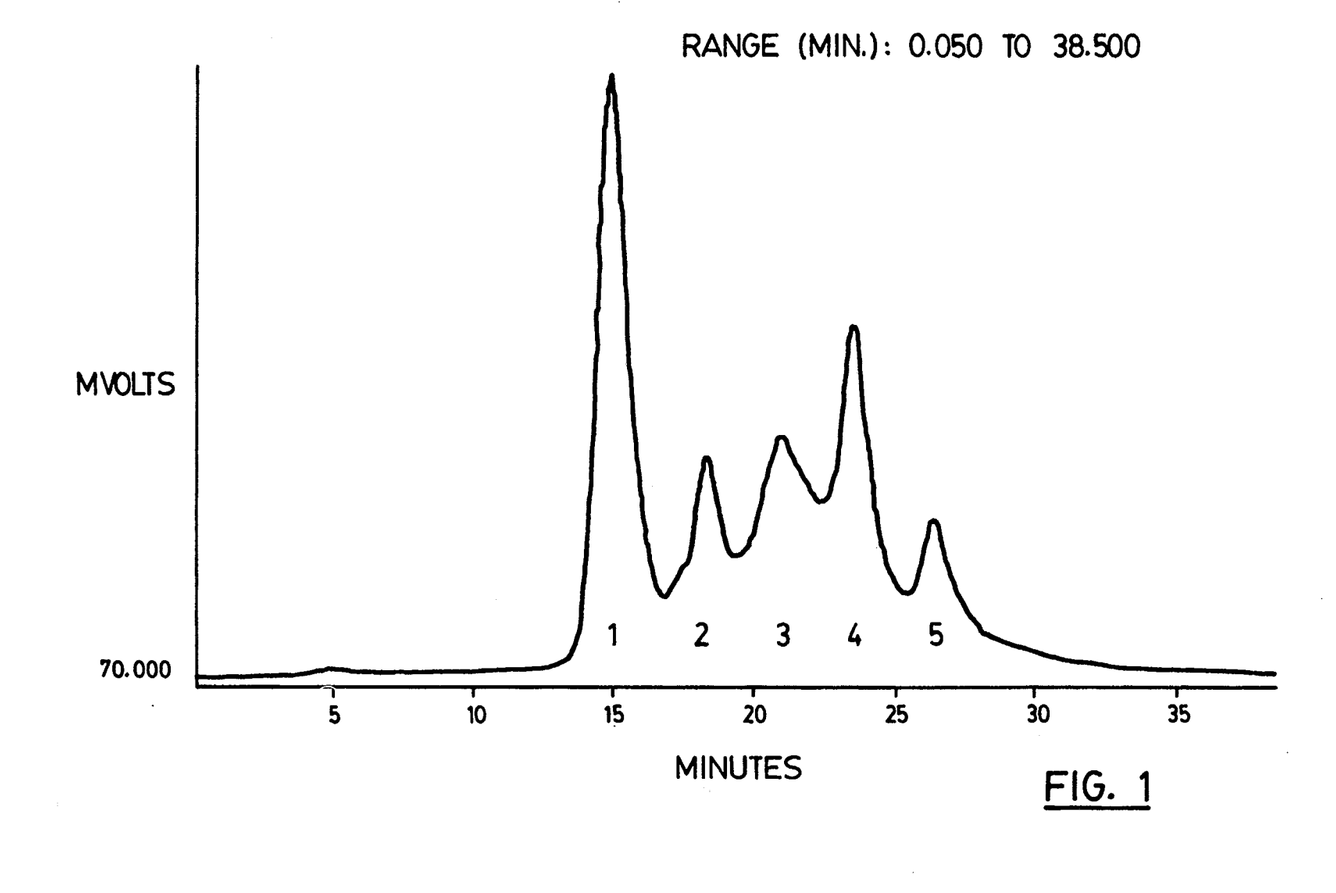
FIG. 1 shows an anion exchange HPLC chromatogram of the reaction mixture after the treatment of deoxyhemoglobin with fumaryl bis(methyl phosphate)
Figure 2:
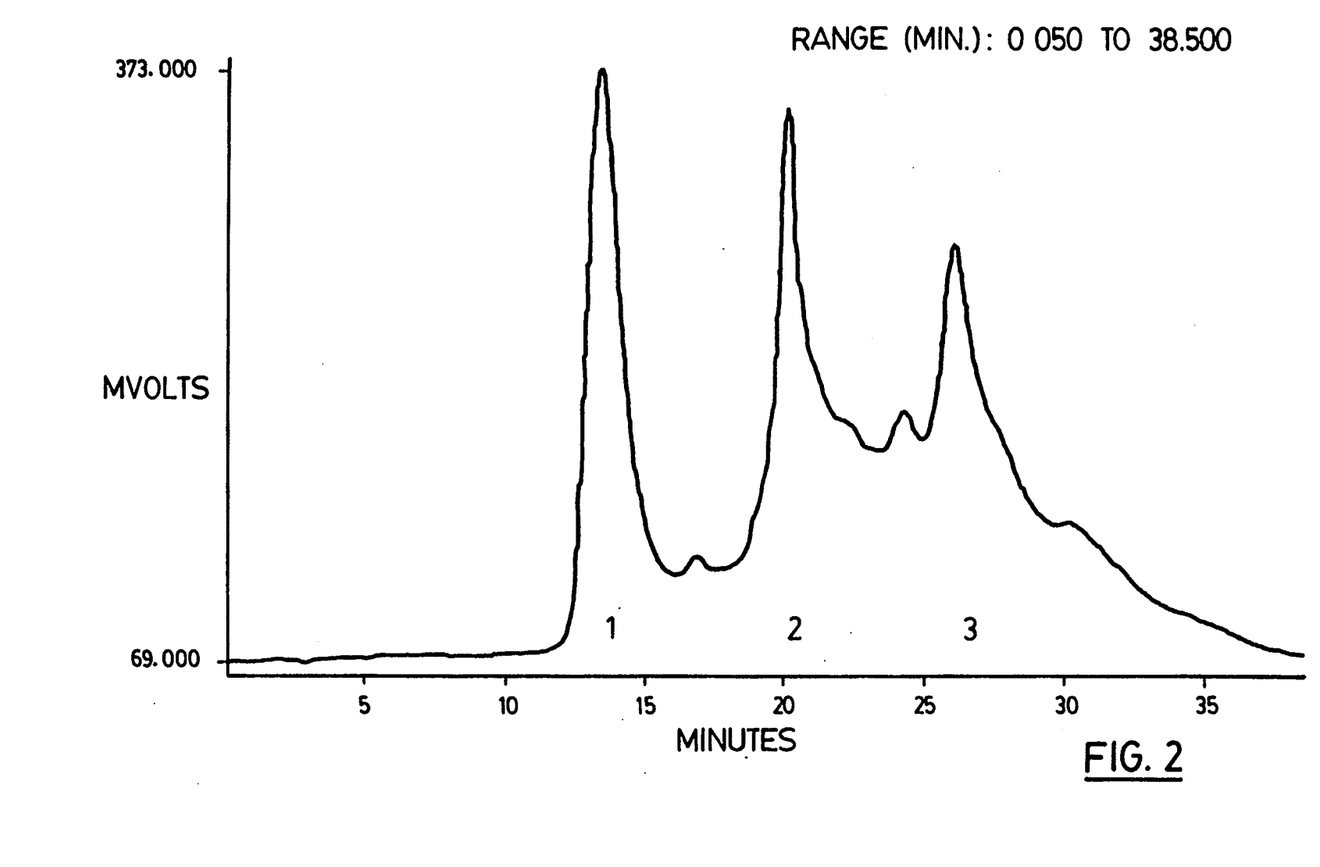
FIG. 2 shows an anion exchange HPLC chromatogram of the reaction mixture after treatment of carbonmonoxyhemoglobin with fumaryl bis(methyl phosphate)
Figure 3:
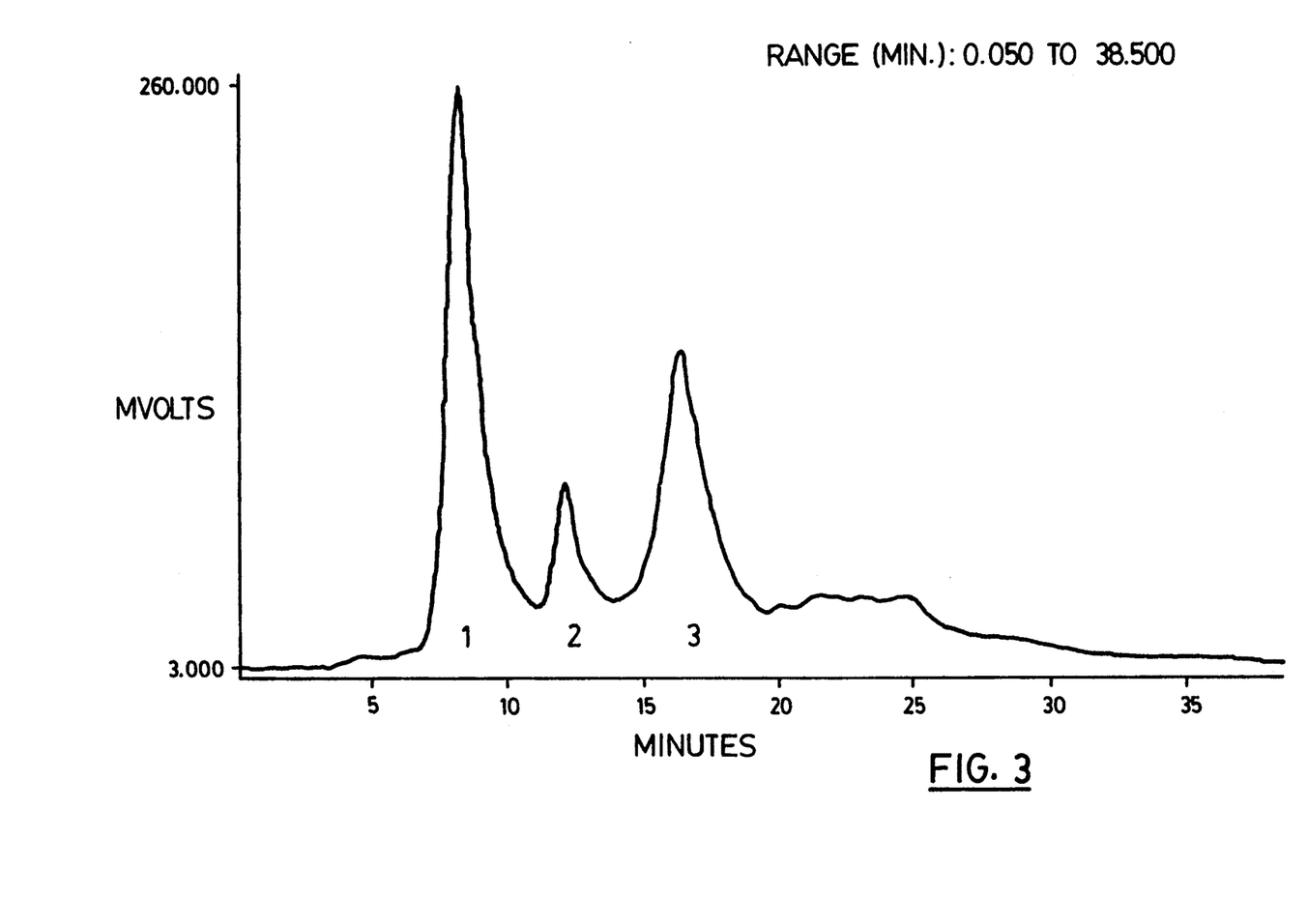
FIG. 3 shows an anion exchange HPLC chromatogram of the reaction products resulting from deoxyhemoglobin treated with fumaryl bis(methyl phosphate) in the presence of 2,3-diphosphoglycerate.
Figure 4:
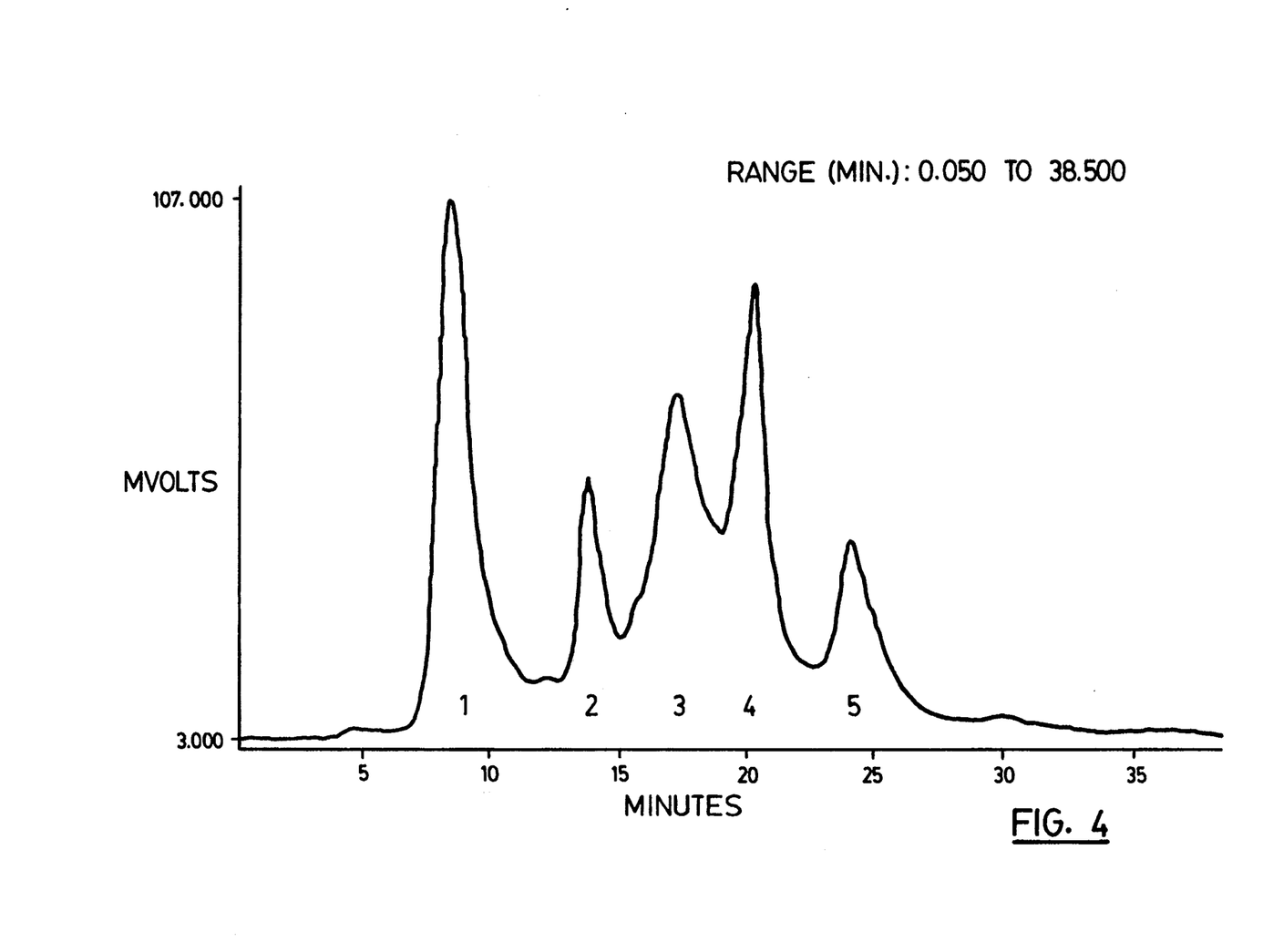
FIG. 4 shows a chromatogram of the reaction mixture after treatment of deoxyhemoglobin with fumaryl bis(methyl phosphate) in the absence of 2,3-diphosphoglycerate.

The number, chromatographic elution positions, and amounts of products of hemoglobin reacted with FMP varies with the ligand state of the hemoglobin and with the presence or absence of 2,3-DPG (2,3, diphosphoglycerate). FIG. 1 is an artion exchange HPLC chromatogram of the reaction mixture after treatment of deoxyhemoglobin with FMP. FIG. 2 is the same using COHb. Zone 1 in each case is the same and represents unreacted Hb A. The second major zone for the COHb is comprised primarily of one of the components found for the third zone for the deoxyHb reaction mixtures. The third major zone in the CohB appears to chromatograph like the last or fifth zone of the deoxyHb mixtures. FIGS. 3 is an artion exchange HPLC chromatogram of the reaction products resulting from deoxyHb treated with FMP in the presence of 2,3-DPG. The elution conditions are slightly different from those used in chromatograms shown in FIGS. 1 and 2. A control of deoxyHb reacted with FMP in the absence of 2,3-DPG using the same chromatographic conditions is shown in FIG. 4. The first zone on each is unreacted Hb A. The second zone in FIG. 3 is not found in either of the other two conditions and contains a modified hemoglobin with a fumaryl bridge between the two $\alpha$-99 lysyl residues. This is the same as the major reaction product found in the product DBBF obtained from Baxter Travenol which is prepared using the bis(3,5-dibromosalicyl) fumarate cross-linker. The third zone in FIG. 3 appears to be a mixture of products containing modifications of both alpha and beta chains but without significant amounts of cross-linked hemoglobins.

The results indicate that the cross-linking site of reaction of human hemoglobin with fumaryl bis(methyl phosphate) is the highly cationic site which binds 2,3-diphosphoglycerate. In the absence of 2,3-diphosphoglycerate, reaction with fumaryl 15 bis(methyl phosphate) produces material that is cross-linked between $\beta$ subunits (val-1 to lys-82) and between the same residues in a single $\beta$ subunit as well as a cross-link between $\alpha$ subunits between lys-99 in each subunit. In the presence of 2,3-diphosphoglycerate, only the $\beta$ cross-link is formed.

EXAMPLE 11

Isophthalyl bis(methyl phosphate) or 3,3'-stilbene bis(methyl phosphate) were reacted with hemoglobin. Modified hemoglobin components were purified on the preparative size Synchropak AX300 and Synchropak CM300 columns using the HPLC system. $\beta_1 1$-$\beta_2 82$ and $\beta_1 82$-$\beta_2 82$ stilbene hemoglobins and $\beta_1 1$-$\beta_2 82$ cross-linked and $\beta_1 1$-$\beta_2 82$ uncross-linked isophthalyl hemoglobins were isolated.

TABLE I

Estimated distance between amino groups that can be crosslinked with monoesters of the compounds of the formula Ib, as calculated from the span of the diamide derived from the dicarboxylic acid.

| Compounds of the Formula Ib | Span of Amine (A°) |
|---|---|
| Fumaryl | 6.1 |
| Isophthalyl | 7.2 |
| Terephthalyl | 7.4 |
| 3,3''-Stilbene | 13.7 |
| 4,4''-Stilbene | 13.9 |

TABLE II
STRUCTURE OF GLOBIN CHAINS FROM PUMARYL BIS (METHYL PHOPHATE) MODIFIED HEMOGLOBINS

| Anion Zone # | Cation Zone # | Chain Zone # | Chain and Modificat |
|---|---|---|---|
| A. Hemoglobins From FMP Treated Deoxyhemoglobin ||||
| AX-1 | CM-1 | I | β-unmodified |
| " | " | II | α-unmodified |
| AX-2 | CM-1 | I | α-unmodified |
| " | " | II | $\beta_1 1$-$\beta_2 82$ |
| AX-3b | CM-1 | I | β-unmodified |
| " | " | II | α-unmodified |
| " | " | III | $\beta_1 1$-$\beta_2 82$ |
| " | " | IV | $\beta_1 1$-$\beta_2 82$ |
| " | " | V | α-modification? |
| " | " | VI | $\alpha_1 99$-$\alpha_2 99$ |
| AX-3b | CM-2 | I | α-unmodified |
| " | " | II | $\beta_1 82$-$\beta_2 82$ |
| AX-3b | CM-3 | I | β-unmodified |
| " | " | II | $\alpha_1 1$-Fumarate? |
| " | " | III | $\beta_1 82$-$\beta_2 82$ |
| AX-3c | CM-1 | I | $\beta_1 1$-Fumarate? |
| " | " | II | α-unmodified |
| AX-3c | CM-2 | I | β-unmodified |
| " | " | II | β-modification? |
| " | " | III | α-unmodified |
| " | " | IV | α-modification? |
| " | " | V | $\alpha_1 99$-$\alpha_2 99$ |
| AX-4 | CM-1 | I | α-unmodified |
| " | " | II | $\beta_1 1$-$\beta_1 82$ |
| AX-5 | CM-1 | I | $\beta_1 82$-Fumarate |
| " | " | II | α-unmodified |
| B. Hemoglobins From FMP Treated Deoxyhemoglobin with 2,3-DPG ||||
| AX-1 | CM-1 | I | β-unmodified |
| " | " | II | α-unmodified |
| AX-2 | CM-1 | I | β-unmodified |
| " | " | II | $\alpha_1 99$-$\alpha_2 99$ |
| AX-3 | CM-1 | I | β-modified? |
| " | " | II | α-modified? |
| C. Hemoglobins From FMP Treated Carbonmonoxyhemoglobin ||||
| AX-1 | CM-1 | I | β-unmodified |
| " | " | II | α-unmodified |
| AX-2 | CM-1 | I | α-unmodified |
| " | " | II | $\beta_1 82$-$\beta_2 82$ |

We claim:

1. A process of preparing a modified, crosslinked hemoglobin comprising:
(a) crosslinking hemoglobin with an acyl phosphate ester crosslinking agent of the formula:

$$R^4 \left[ \begin{array}{c} O \quad O \\ \| \quad \| \\ C-O-P-OR \\ | \\ OCH_3 \end{array} \right]_n \quad (V)$$

where n is an integer from 2-5;
R is methyl, ethyl, benzyl or an alkali metal counterion;
and $R^4$ is a linear or branched alkyl, alkenyl, alkynyl, cyclic alyl, cyclic alkenyl, aryl, arylalkenyl, arylalkyl or aryl substituted by alkyl, alkenyl or alkynyl; and (b) purifying the resulting crosslinked hemoglobin.

2. The process of claim 1 wherein the crosslinking reaction is conducted at a pH of from about 5 to 8.

3. The process of claim 2 wherein the crosslinking reaction is conducted at a temperature of from about 0° C. to 50° C.

4. The process of claim 1 wherein the hemoglobin in the crosslinking reaction is liganded hemoglobin.

5. The process of claim 1 wherein the hemoglobin in the crosslinking reaction is deoxyhemoglobin.

6. The process of claim 1 wherein the acyl phosphate ester crosslinking reagent has the general formula (V) in which n is an integer 2 or 3, $R^4$ represents a linear alkenyl, phenyl, diphenylalkenyl, benzyl or naphthyl group and R is an alkali metal counterion.

7. The process of claim 6 wherein the acyl phosphate ester crosslinking agent is a fumaryl bismethyl phosphate) of formula:

$$\begin{array}{c} O \quad\quad\quad\quad\quad\quad\quad O \\ \| \quad\quad\quad\quad\quad\quad\quad \| \\ RO-P-O-C-CH=CH-C-O-P-OR \\ | \quad \| \quad\quad\quad\quad\quad \| \quad | \\ OCH_3 \; O \quad\quad\quad\; O \; OCH_3 \end{array}$$

wherein R is methyl or an alkali metal counterion.

8. The process of claim 6 wherein the acyl phosphate ester crosslinking agent is an isophthalyl methyl phosphate of the formula:

$$CH_3-O-\overset{O}{\underset{OR}{\overset{\|}{P}}}-O-\overset{O}{\overset{\|}{C}}-\underset{\underset{O=P-OR}{\overset{O}{\underset{\|}{\underset{\|}{C=O}}}}}{\bigcirc}$$
$$\quad\quad\quad\quad\quad\quad\quad\quad\quad\quad\quad OCH_3$$

wherein R is methyl or an alkali metal counterion.

9. The process of claim 6 wherein the acyl phosphate ester crosslinking agent is a terephthalyl methyl phosphate of the formula:

$$CH_3O-\overset{O}{\underset{OR}{\overset{\|}{P}}}-O-\overset{O}{\overset{\|}{C}}-\bigcirc-\overset{O}{\overset{\|}{C}}-O-\overset{OR}{\underset{O}{\overset{|}{P}}}-OCH_3$$

where R is methyl or an alkali metal counterion.

10. The process of claim 6 wherein the acyl phosphate ester crosslinking agent is a stilbene 3,3'dicarboxylic acid methyl phosphate of the formula:

$$CH_3O-\overset{OR}{\underset{O}{\overset{|}{P}}}-O-\overset{O}{\overset{\|}{C}}-\bigcirc-\underset{H}{\overset{H}{\underset{|}{C}}}=\underset{|}{\overset{|}{C}}-\bigcirc-\overset{O}{\overset{\|}{C}}-O-\overset{OR}{\underset{O}{\overset{|}{P}}}-OCH_3$$

where R is methyl or an alkali metal counterion.

11. The process of claim 6 wherein the acyl phosphate ester crosslinking agent is a stilbene 4,4'-dicarboxylic acid methyl phosphate of the formula:

where R is methyl or an alkali metal counterion.

12. The process of claim 6 wherein the acyl phosphate ester crosslinking agent is benzene 1,3,5-tricarboxylic acid tris(sodium methyl phosphate).

* * * * *